United States Patent
Schäfer et al.

(10) Patent No.: US 6,538,139 B1
(45) Date of Patent: Mar. 25, 2003

(54) PREPARATION OF PYRROLE AND PYRIDINE

(75) Inventors: Martin Schäfer, Grünstadt (DE); Arnd Böttcher, Frankenthal (DE); Andreas Kramer, Bad Dürkheim (DE); Arthur Höhn, Kirchheim (DE); Reinhard Kaczmarek, Hassloch (DE); Erhard Henkes, Einhausen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/234,169

(22) Filed: Sep. 5, 2002

(30) Foreign Application Priority Data

Sep. 11, 2001 (DE) .......................... 101 44 631

(51) Int. Cl.⁷ .................. C07D 213/133; C07D 207/32
(52) U.S. Cl. ....................... 546/252; 548/564
(58) Field of Search ........................ 546/252; 548/564

(56) References Cited

U.S. PATENT DOCUMENTS

| 3,522,269 A | 7/1970 | Guyer et al. ................. 260/313 |
| 4,762,929 A | 8/1988 | Rebafka ..................... 546/252 |

FOREIGN PATENT DOCUMENTS

| EP | 67 360 | 12/1982 |
| EP | 0 155 649 | 9/1985 |
| GB | 1 393 086 | 5/1975 |

*Primary Examiner*—Patricia L. Morris
(74) *Attorney, Agent, or Firm*—Keil & Weinkauf

(57) ABSTRACT

Pyrroles of the formula (I)

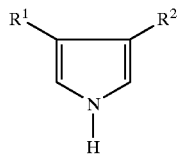

are prepared by dehydrogenating pyrrolidines of the formula (II)

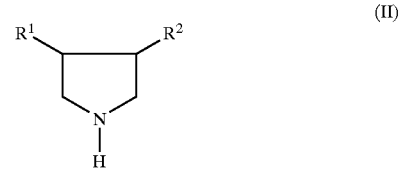

where $R^1$ and $R^2$, independently of one another, are hydrogen or an aliphatic radical of 1 to 6 carbon atoms, or pyridines of the formula (III)

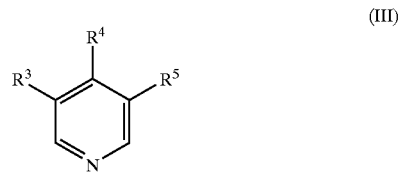

are prepared by dehydrogenating piperidines of the formula (IV)

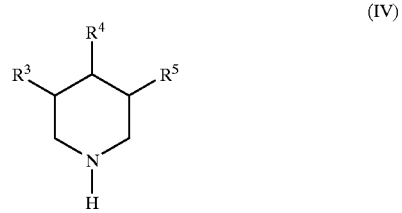

where $R^3$, $R^4$ and $R^5$, independently of one another, are hydrogen or an aliphatic radical of 1 to 6 carbon atoms, in the presence of a supported noble metal catalyst, by a process in which the dehydrogenation is carried out in the presence of from 1 to 50% by weight, based on the pyrrolidine or piperidine and water, of water.

8 Claims, No Drawings

PREPARATION OF PYRROLE AND PYRIDINE

The present invention relates to the preparation of pyrroles from pyrrolidines and of pyridines from piperidines by dehydrogenation over noble metal catalysts.

It is known that pyrrolidine and piperidine can be dehydrogenated over palladium- and/or platinum-containing supported catalysts to give pyrrole and pyridine, respectively.

U.S. Pat. No. 3 522 269 describes the dehydrogenation of pyrrolidine to pyrrole over Pd catalysts at relatively high temperatures, preferably 400–450° C.

GB-A 1 393 086 describes the dehydrogenation of piperidine to pyridine by means of catalysts comprising palladium on $SiO_2$ as a support.

EP-A 67 360 and 155 649 describe Pd catalysts for dehydrogenating pyrrolidines, which are effective at lower temperatures of from 160 to 400° C.

In the dehydrogenation of pyrrolidine to pyrrole, a certain amount of byproducts, such as butylamine, N-butylpyrrole and butyronitrile, is formed. Among these, butyronitrile, which is generally formed in amounts of from 0.3 to 3% by weight, is particularly troublesome. Owing to the very similar boiling points of pyrrole and butyronitrile, butyronitrile can be separated from pyrrole by distillation only with considerable effort. Columns having a large number of theoretical plates are required for this purpose, and a high reflux ratio has to be employed. The distillative separation is associated with a large loss of desired product. However, the use of the pyrroles in the preparation of pharmaceutical active compounds or in electronic components requires very high purity of the pyrroles.

It i s a n object of the present invention to provide an improved process for the preparation of pyrroles and pyridines in which byproducts are formed to a smaller extent.

We have found that this object is achieved by a process for the preparation of pyrroles of the formula (I)

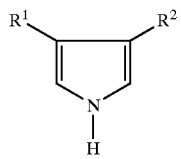

(I)

where
$R^1$ and $R^2$, independently of one another, are hydrogen or an aliphatic radical of 1 to 6 carbon atoms,
by dehydrogenating pyrrolidines of the formula (II)

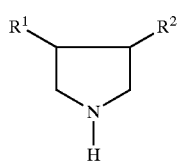

(II)

where $R^1$ and $R^2$ have the abovementioned meanings,
in the presence of a supported noble metal catalyst, wherein the dehydrogenation is carried out in the presence of from 1 to 50% by weight, based on pyrrolidine and water, of water.

It has been found that the formation of (substituted) butyronitrile is greatly suppressed by the presence of water during the dehydrogenation of (substituted) pyrrolidine. The amount of butyronitrile in the crude discharge of the dehydrogenation of pyrrolidine is in general <0.2, preferably <0.1, % by weight. As a result, the subsequent purification of pyrrole by distillation is considerably simplified. Large losses of desired product do not occur, making the preparation of pyrrole as a whole more economical.

Suitable pyrrolidines (I) are unsubstituted pyrrolidine and pyrrolidine which is substituted in the 3- and/or 4-position by an aliphatic radical of 1 to 6 carbon atoms. The aliphatic radicals may be substituted by groups which are inert under the reaction conditions. Preferred aliphatic radicals are methyl, ethyl, propyl, isopropyl, butyl, isobutyl, sec-butyl, tert-butyl and isomeric pentyl and hexyl radicals. A preferred starting compound of the novel dehydrogenation is unsubstituted pyrrolidine.

In the same way, the preparation of pyridines of the formula (III)

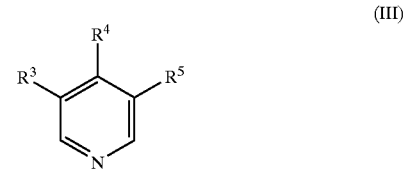

(III)

can be carried out by dehydrogenating piperidines of the formula (IV)

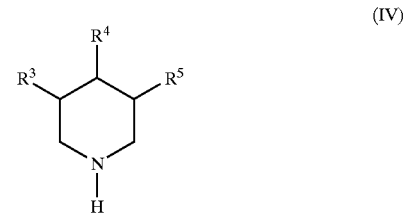

(IV)

Therein, $R^3$, $R^4$ and $R^5$, independently of one another, may have the same meanings as $R^1$ and $R^2$. Unsubstituted piperidine is preferred. As a result of the presence of water during the dehydrogenation, the formation of (substituted) valeronitrile as a byproduct is accordingly suppressed.

The dehydrogenation is carried out in the presence of from 1 to 50, preferably from 5 to 50, particularly preferably from 5 to 25, % by weight of water. The percentage data are based on the sum of pyrrolidine or piperidine and water, which gives 100% by weight. The water may have been admixed with the pyrrolidine or piperidine feedstock stream or may be fed into the reactor during the dehydrogenation in the corresponding ratio.

The novel catalytic dehydrogenation can be carried out in the liquid phase or in the gas phase.

The novel catalytic dehydrogenation can be carried out in the liquid phase. For this purpose, pyrrolidine or piperidine and the noble metal-containing supported catalyst, if required in a solvent, are kept at the reaction temperature, for example for from 1 to 10 hours. The catalyst is separated from the resulting product mixture by filtration, and pyrrole or pyridine is obtained by fractional distillation. Preferred solvents are toluene, xylenes, diethylbenzene, ethanol, n-butanol, methyl glycol, ethylene glycol and 1,2-dimethoxyethane. The dehydrogenation in the liquid phase is usually carried out in the presence of small amounts of hydrogen in order to activate the catalyst.

The novel dehydrogenation is preferably carried out continuously in the gas phase, it being possible to arrange the catalyst in a fixed bed or as a fluidized bed.

If the novel dehydrogenation is carried out in the gas phase, the pyrrolidine/steam mixture or piperidine/steam mixture is preferably present in a carrier gas stream comprising nitrogen and/or hydrogen. The volume ratio carrier gas: pyrrolidine or piperidine is as a rule from 1:1 to 100:1, preferably from 2:1 to 50:1, particularly preferably from 3:1 to 40:1. The volume ratio of nitrogen to hydrogen may be from 0.01:1 to 100:1, preferably from 0.1:1 to 10:1, particularly preferably from 0.5:1 to 5:1.

The novel dehydrogenation can be carried out in the presence of all noble metal-containing supported catalysts which are customary for this dehydrogenation reaction. In general, temperatures of from 150 to 400° C. and pressures of from 0.01 to 50 bar are employed.

The novel dehydrogenation can be carried out, for example, in the presence of the palladium supported catalysts which are described in EP-A 0 067 360 and contain basic compounds and/or elements of group 11, group 12 and group 7, cobalt and/or nickel. Supports are, for example, alumina, silica, aluminum silicate, magnesium silicate or spinels of aluminum, of chromium or of iron. Preferred activating additional elements of groups 7, 11 and 12 are manganese, zinc and silver. Preferred basic compounds are the oxides, hydroxides or carbonates of the alkali metals, preferably of lithium, of the alkaline earth metals, preferably of magnesium and of calcium, and of the lanthanides, preferably of cerium, of praesodynium and of neodynium.

However, noble metal-containing catalysts which contain from 30 to 100% by weight of a) palladium on an oxide of a rare earth metal or an oxide of an element of group 4 or b) a platinum/palladium mixture on alumina, an oxide of a rare earth metal or an oxide of an element of group 4 and from 0 to 70% by weight of alkali metal oxide or alkaline earth metal oxide are preferred. In the presence of these catalysts, the novel dehydrogenation is generally carried out at from 150 to 300° C., preferably from 170 to 270° C., particularly preferably from 180 to 250° C., and from 0.01 to 50, preferably from 0.1 to 5, particularly preferably from 1 to 1.5, bar.

In the context of this description, suitable rare earth metals are the elements of the lanthanide and the actinide group of the Periodic Table of the Elements, such as lanthanum, cerium, neodynium, samarium, gadolinium, ytterbium, actinium, thorium, uranium and neptunium, cerium, praesodynium, neodynium, samarium, europium, terbium, ytterbium, thorium and protactinium being preferred, and cerium, praesodynium, neodynium and thorium being particularly preferred.

Suitable metals of group 4 are titanium, zirconium and hafnium, titanium and zirconium being preferred, and zirconium being particularly preferred. Suitable alkali metals or alkaline earth metals are lithium, sodium, potassium, cesium, beryllium, magnesium, calcium, strontium and barium, sodium, potassium, magnesium, calcium and barium being preferred.

The active components of the catalyst (noble metals) are preferably present on oxides of the lanthanides or actinides or on oxides of elements of group 4 when the active component is pure palladium, and preferably on supports substantially comprising alumina, on oxides of the rare earth metals or on oxides of group 4 when the active component is a platinum/palladium mixture.

The catalysts can, if present, be prepared by kneading of the additives (i.e. of the alkali metal or alkaline earth metal oxides) together with the support material, thermal after-treatment (heating) at from 400 to 900° C. and impregnation with a solution containing a salt of the noble metal, or by impregnation of the support with a solution of the additives and of the noble metal, for example in the form of solutions of their nitrates, chlorides, formates, oxalates or ammoniates and subsequent heating at from 400 to 900° C. If spinel formation is to be effected, a temperature of from 900 to 1300° C. must be reached after the kneading or the impregnation of the alumina with the oxide or the solution of the additive component (cf. Ullmanns Encyklopädie der technischen Chemie, 3rd Edition (1955), Volume 6, pages 242 to 244).

The noble metal content of the catalysts is as a rule from 0.0001 to 25, preferably from 0.001 to 20, particularly preferably from 0.05 to 15, % by weight, based on the support material. The catalysts can be used, for example, in the form of moldings, e.g. extrudates, tablets or rings, or as powder, depending on the intended use. The preferably used catalysts have the advantage that they are more slowly deactivated and that, through their use during the dehydrogenation in industrial operation, substantially fewer stoppages or downtimes are therefore required for catalyst change. They have a high initial selectivity for the dehydrogenation to give the aromatic heterocycle, so that their selectivity is also very good over the total time-on-stream with a catalyst batch. The formation of pyrrolines as byproducts can be substantially suppressed.

The reaction is preferably carried out in a tubular reactor since it is important to avoid back-mixing from the exit of the plant, i.e. the end of the last reaction zone, to the entrance, i.e. the beginning of the first reaction zone, which can most easily be achieved in tubular reactors and the plug flow forming therein.

Water is separated from the resulting product mixture by phase separation, for example in a mixer-settler apparatus. Pyrrole and pyridine, which may still contain unconverted pyrrolidine and piperidine, respectively, and byproducts, are then subjected to purification by distillation.

The compounds prepared by the novel process can be used, for example, for the preparation of pharmaceutical active compounds. The pyrroles prepared according to the invention can be used in particular in electrolytic capacitors. Pyrroles and pyridines are useful intermediates for organic synthesis.

The examples which follow illustrate the invention.

EXAMPLES

The dehydrogenations were carried out in an electrically heated gas-phase laboratory reactor which had been filled with a supported platinum/palladium catalyst (0.5% by weight of Pt/0.5% by weight of Pd on $ZrO_2$). The reactor had a diameter of 30 mm and a length of 1000 mm and the length of the catalyst bed was 350 mm. The pyrrolidine feedstock stream was mixed with the amount of water stated in the table before the dehydrogenation. The reaction was carried out at atmospheric pressure and at 260° C. in a gas stream comprising 75% by volume of $H_2$ and 25% by volume of $N_2$. 0.05 l of feed comprising pyrrolidine/water per liter of catalyst per hour was metered into 50 l(S.T.P.)/h of the gas stream via an evaporator. After the reactor, the reaction products were condensed out by means of a jacketed coil condenser with downstream cold trap and were analyzed by gas chromatography.

The test results are summarized in the table below.

TABLE

| H$_2$O [% by wt.] | Pyrrole [GC %] | Pyrrol- idine [GC %] | N-Butyl- pyrrole [GC %] | Butyl- amine [GC %] | Butyro- nitrile [GC %] | Butyro- nitrile/ Pyrrole [GC %] |
|---|---|---|---|---|---|---|
| 5  | 82 | 4  | 4.2 | 1.4 | 0.13 | 0.15 |
| 10 | 83 | 6  | 2.7 | 1.8 | 0.09 | 0.10 |
| 15 | 79 | 11 | 1.3 | 2.5 | 0.05 | 0.06 |
| —* | 78 | 8  | 1.8 | 3.0 | 0.30 | 0.38 |

*Comparative example

As shown in the table, as little as 5% by weight of water in the feedstock stream lead to a considerable reduction in the butyronitrile formation compared with the comparative example. At a water content of 15% by weight, the butyronitrile concentration is only a sixth of that which is obtained when working in the absence of water.

We claim:

1. A process for the preparation of pyrroles of the formula (I)

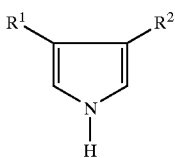

(I)

by dehydrogenating pyrrolidines of the formula (II)

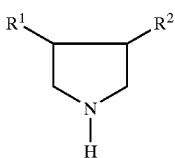

(II)

where

R$^1$ and R$^2$, independently of one another, are hydrogen or an aliphatic radical of 1 to 6 carbon atoms, or of pyridines of the formula (III)

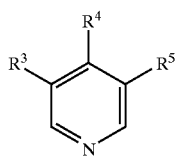

(III)

by dehydrogenating piperidines of the formula (IV)

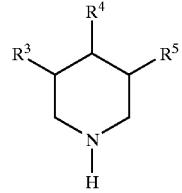

(IV)

where

R$^3$, R$^4$ and R$^5$, independently of one another, are hydrogen or an aliphatic radical of 1 to 6 carbon atoms,
in the presence of a supported noble metal catalyst, wherein the dehydrogenation is carried out in the presence of from 1 to 50% by weight, based on the pyrrolidine or piperidine and water, of water.

2. A process as claimed in claim 1, wherein the dehydrogenation is carried out in the liquid phase or in the gas phase.

3. A process as claimed in claim 1, wherein the dehydrogenation is carried out in the gas phase in the presence of hydrogen in an amount of from 1 to 100 mol per mol of pyrrolidine or piperidine.

4. A process as claimed in claim 1, wherein the dehydrogenation is carried out at from 150 to 400° C. and from 0.01 to 50 bar.

5. A process as claimed in claim 1, wherein the noble metal catalyst contains from 30 to 100% by weight of
   a) palladium on an oxide of a rare earth metal or an oxide of an element of group 4 of the Periodic Table of the Elements or
   b) a platinum/palladium mixture on alumina, an oxide of a rare earth metal or an oxide of an element of group 4, and from 0 to 70% by weight of alkali metal or alkaline earth metal oxide.

6. A process as claimed in claim 5, wherein an oxide of cerium, of praesodynium, of neodynium, of samarium, of europium, of terbium, of ytterbium, of thorium or of protactinium is used as the oxide of a rare earth metal.

7. A process as claimed in claim 5, wherein an oxide of titanium or of zirconium is used as the oxide of an element of group 4.

8. A process as claimed in claim 5, wherein an oxide of sodium, of potassium, of magnesium, of calcium or of barium is used as the alkali metal or alkaline earth metal oxide.

* * * * *